US011350892B2

(12) United States Patent
Budde et al.

(10) Patent No.: US 11,350,892 B2
(45) Date of Patent: Jun. 7, 2022

(54) COLLIMATOR STRUCTURE FOR AN IMAGING SYSTEM

(71) Applicant: General Electric Company, Schenectady, NY (US)

(72) Inventors: Adam Budde, Middleton, WI (US); Mark Adamak, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 1076 days.

(21) Appl. No.: 15/381,893

(22) Filed: Dec. 16, 2016

(65) Prior Publication Data
US 2018/0168522 A1    Jun. 21, 2018

(51) Int. Cl.
*A61B 6/06*  (2006.01)
*A61B 6/00*  (2006.01)
*A61B 6/03*  (2006.01)

(52) U.S. Cl.
CPC ............... *A61B 6/06* (2013.01); *A61B 6/032* (2013.01); *A61B 6/4291* (2013.01); *A61B 6/4233* (2013.01)

(58) Field of Classification Search
CPC ......... A61B 6/06; A61B 6/032; A61B 6/4291; A61B 6/4233; G21K 1/02; G21K 1/067; G21K 1/025; G21K 2201/067; G06T 2207/10076; G01T 1/2006
See application file for complete search history.

(56) References Cited

U.S. PATENT DOCUMENTS

| | | | |
|---|---|---|---|
| 5,606,589 A * | 2/1997 | Pellegrino | A61B 6/502 378/147 |
| 5,864,598 A | 1/1999 | Hsieh et al. | |
| 6,304,632 B1 * | 10/2001 | Rick | G21K 1/025 378/155 |
| 6,365,900 B1 * | 4/2002 | Mestais | G01T 1/1642 250/363.1 |
| 6,429,434 B1 * | 8/2002 | Watson | G01T 1/1648 250/363.04 |
| 6,438,195 B1 | 8/2002 | Hsieh | |

(Continued)

OTHER PUBLICATIONS

Ismailova, E., "Apodized-Aperture Pixel Design X-Ray Detector for Improvement of Detective Quantum Efficiency at High Spatial Frequencies," Electronic Thesis and Dissertation Repository, University of Western Ontario Graduate Program in Medical Biophysics, Nov. 2015, 61 pages.

*Primary Examiner* — Dani Fox
*Assistant Examiner* — Soorena Kefayati
(74) *Attorney, Agent, or Firm* — McCoy Russell LLP

(57) ABSTRACT

Methods and systems are provided for reducing aliasing artifacts in images generated in an imaging system, such as a computed tomography (CT) imaging systems. In one embodiment, a method comprises receiving a filtered signal generated by passing a primary signal through a collimator having a non-rectangular transition profile, the collimator positioned between an object and a detector of an imaging system, and generating an image based on the filtered signal received at the detector, the primary signal including radiation from a source of the imaging system attenuated by the object placed between the source and the detector. In this way, by filtering the signals at the collimator before reaching the detector, aliasing artifacts in the images may be reduced.

12 Claims, 11 Drawing Sheets

(56) References Cited

U.S. PATENT DOCUMENTS

| | | | | |
|---|---|---|---|---|
| 6,980,629 B1* | 12/2005 | Hoheisel | ............... | G21K 1/10 378/149 |
| 7,313,214 B2* | 12/2007 | Bruder | ............... | A61B 6/032 378/15 |
| 7,655,915 B2* | 2/2010 | Ratzmann | ............ | G01T 1/1648 250/367 |
| 2002/0122532 A1* | 9/2002 | Mioitti | ............... | A61B 6/4291 378/155 |
| 2002/0196902 A1* | 12/2002 | Miotti | ............... | A61B 6/4291 378/155 |
| 2004/0120464 A1* | 6/2004 | Hoffman | ............ | G21K 1/025 378/147 |
| 2004/0251420 A1* | 12/2004 | Sun | ............... | G01T 1/202 250/370.09 |
| 2005/0207630 A1* | 9/2005 | Chan | ............... | A61B 6/466 382/131 |
| 2006/0233298 A1* | 10/2006 | Igarashi | ............ | A61B 6/032 378/19 |
| 2006/0251212 A1* | 11/2006 | Blanz | ............... | A61B 6/4233 378/62 |
| 2007/0086565 A1* | 4/2007 | Thompson | ............ | A61B 6/032 378/19 |
| 2008/0170665 A1* | 7/2008 | Marar | ............... | A61B 6/02 378/91 |
| 2009/0001273 A1* | 1/2009 | Hawman | ............ | G21K 1/025 250/363.04 |
| 2009/0022279 A1* | 1/2009 | Wieczorek | ............ | G21K 1/025 378/154 |
| 2009/0033940 A1* | 2/2009 | Sanpitak | ............ | A61B 6/037 356/432 |
| 2009/0225938 A1* | 9/2009 | Zeitler | ............... | G01T 1/2985 378/51 |
| 2012/0172700 A1* | 7/2012 | Krishnan | ............ | G16H 30/20 600/407 |
| 2012/0307963 A1* | 12/2012 | Watanabe | ............ | G21K 1/025 378/7 |
| 2012/0321041 A1* | 12/2012 | Ikhlef | ............... | G21K 1/025 378/62 |
| 2013/0077738 A1* | 3/2013 | Kreisler | ............ | A61B 6/03 378/7 |
| 2013/0308748 A1* | 11/2013 | Ikhlef | ............... | A61B 6/03 378/19 |
| 2013/0315373 A1* | 11/2013 | Rossl | ............... | G21K 1/06 378/62 |
| 2014/0042333 A1* | 2/2014 | Niederlohner | ....... | A61B 6/4233 250/394 |
| 2014/0138556 A1* | 5/2014 | Shahar | ............... | A61B 6/4291 250/394 |
| 2014/0153691 A1* | 6/2014 | Kurochi | ............... | A61B 6/032 378/19 |
| 2014/0177781 A1* | 6/2014 | Singh | ............... | G21K 1/02 378/4 |
| 2014/0241493 A1* | 8/2014 | Yokoyama | ............ | C25D 5/34 378/36 |
| 2014/0341355 A1* | 11/2014 | Hsieh | ............... | A61B 6/4014 378/149 |
| 2014/0355734 A1* | 12/2014 | Ying | ............... | G01T 1/1648 378/7 |
| 2015/0078525 A1* | 3/2015 | Hofmann | ............ | H01L 27/14601 378/62 |
| 2015/0324973 A1* | 11/2015 | Ueki | ............... | G01T 1/24 382/132 |
| 2016/0170038 A1* | 6/2016 | Yu | ............... | G01T 1/17 250/394 |
| 2017/0265822 A1* | 9/2017 | Du | ............... | A61B 6/03 |
| 2017/0269008 A1* | 9/2017 | Sjolin | ............... | G01T 1/17 |
| 2017/0269236 A1* | 9/2017 | Wirth | ............... | A61B 6/4233 |
| 2018/0120450 A1* | 5/2018 | Tashiro | ............... | G21K 1/025 |
| 2018/0140269 A1* | 5/2018 | Roessl | ............... | A61B 6/484 |

* cited by examiner

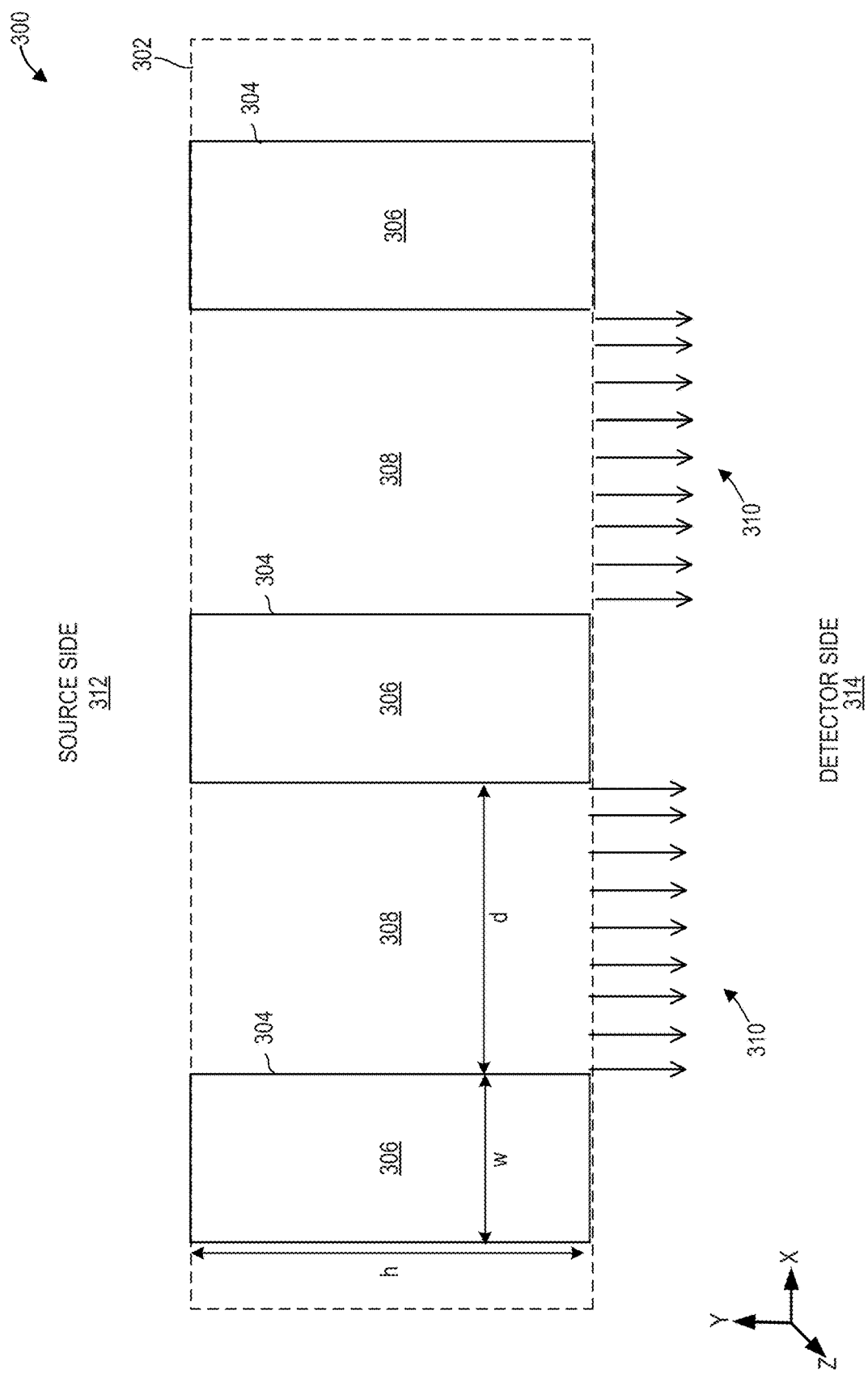

COLLIMATOR STRUCTURE FOR AN IMAGING SYSTEM

FIELD

Embodiments of the subject matter disclosed herein relate to non-invasive diagnostic imaging, and in some examples, to a collimator of a computed tomography (CT) imaging system that attenuates radiation signals in a non-uniform manner.

BACKGROUND

Non-invasive imaging technologies allow images of the internal structures of an object (e.g., patient) to be obtained without performing an invasive procedure on the object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

In CT imaging systems, a source projects a beam (e.g., x-ray beam), which passes through an object being imaged, and impinges upon an array of detectors. As such, the beam is attenuated by the object, and the intensity of the beam received at the array of detectors depends on the amount by which the beam is attenuated by the object. The attenuated beam is then used to reconstruct the tomographic images.

Typically, the CT imaging systems include a pre-patient collimator positioned proximate to the source that defines the profile of the beam passing through the object. In addition, the CT imaging systems include a post-patient collimator positioned in front of the array of detectors to shield the detectors from scattered radiation.

Generally, the post-patient collimator used in CT imaging systems includes a rectangular spatial profile. In some examples, the post-patient collimator may be formed with a high attenuation material such as tungsten or lead. Specifically, the post-patient collimator may include open regions (or low attenuation regions) in between high attenuation regions forming a grid-like pattern. As such, a portion of the beam passes through the open regions and reaches the detectors, and the remaining portion of the beam is blocked by the high attenuation regions. In this way, the post-patient collimator may control the amount of radiation reaching the detector, reduce unwanted scattered radiation from reaching the detector, and thereby reduce noise in the systems. However, such post-collimators may lead to a spatial domain response of the detector that may cause high frequency components in the signal to wrap around and form aliasing artifacts in the final CT images that reduces the quality of the CT images.

BRIEF DESCRIPTION

In one embodiment, a method comprises receiving a filtered signal generated by passing a primary signal through a collimator having a non-rectangular transition profile, the collimator positioned between an object and a detector of an imaging system, and generating an image based on the filtered signal received at the detector, the primary signal including radiation from a source of the imaging system attenuated by the object placed between the source and the detector. Herein, the non-rectangular transition profile of the collimator may modulate the primary signal before the signal reaches the detector. As such, modulating the primary signal results in filtering the analog signals in a spatial domain of the collimator and reducing high frequency components of the primary signal, even before reaching the detector. In this way, by pre-filtering the signals and reducing high frequency components of the signals, aliasing artifacts in the CT images may be reduced.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 3A shows the post-patient collimator having a rectangular transition profile, according to an embodiment of the invention;

DETAILED DESCRIPTION

The following description relates to various embodiments of medical imaging systems. In particular, methods and systems are provided for reducing aliasing artifacts in the imaging systems. An example of a computed tomography (CT) imaging system that may be used to acquire images processed in accordance with the present techniques is provided in FIGS. 1 and 2. The CT imaging system may include a pre-patient collimator positioned in between a source and a patient that is being scanned, and further includes a post-patient collimator or anti-scatter collimator positioned in front of a detector (FIG. 2). While the pre-patient collimator adjusts the width of a source beam, the post-patient collimator controls the width of an attenuated beam after passing through the patient before reaching the detector. Typically, the post-patient collimator includes a rectangular transition profile as shown in FIG. 3A, having low attenuation regions or plates juxtaposed to high attenuation regions or plates. However, the rectangular profile of the post-patient collimator may lead to aliasing artifacts in the CT image. Herein, the aliasing artifacts are caused due to higher frequencies in the signal wrapping around and contaminating the signal detected by the detector as shown in an example CT image in FIG. 6.

Figure 3B:
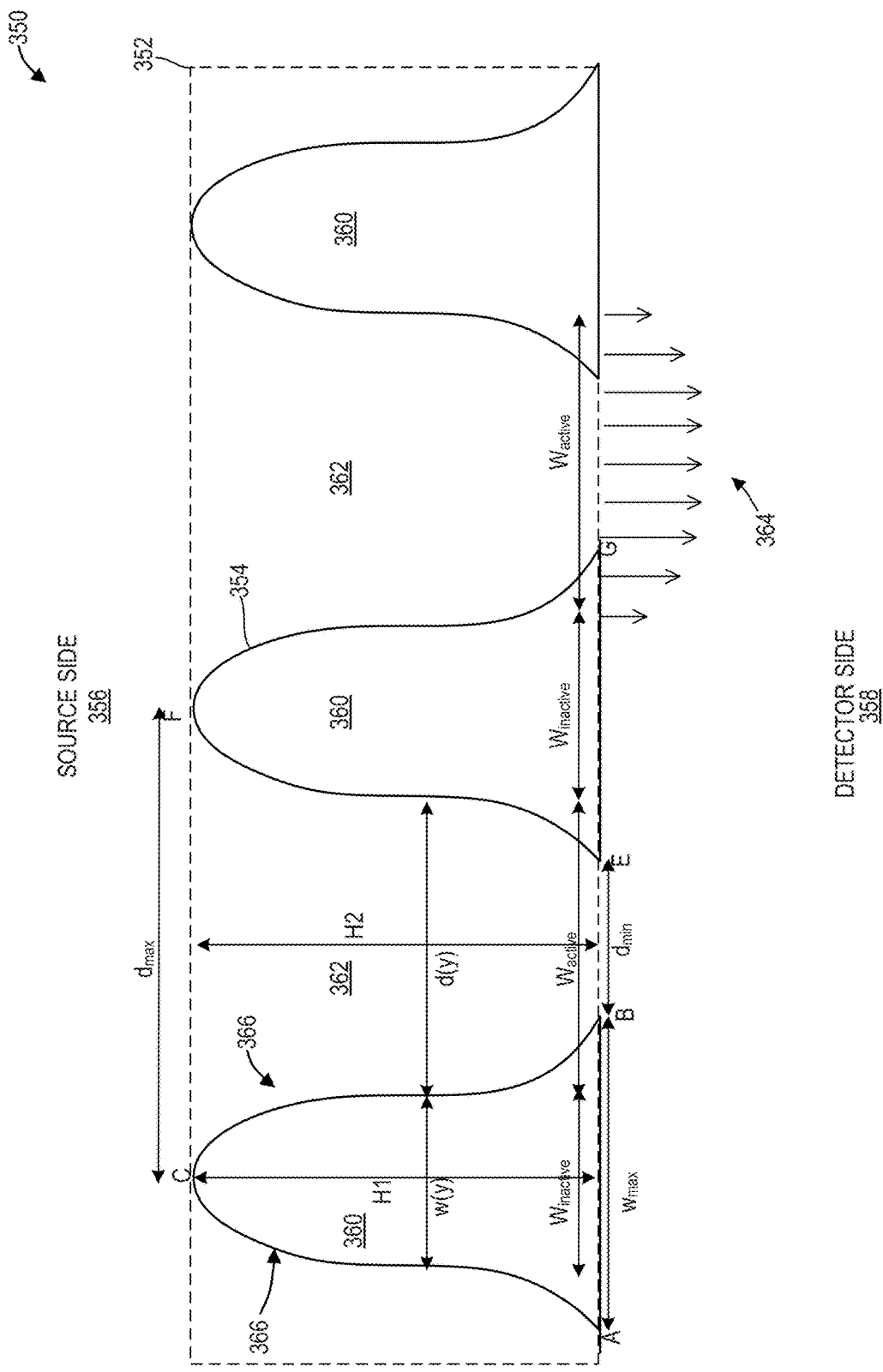
FIG. 3B shows the post-patient having an anti-aliasing shape resulting in a modulated transition profile, according to an embodiment of the invention.
Figure 4B:
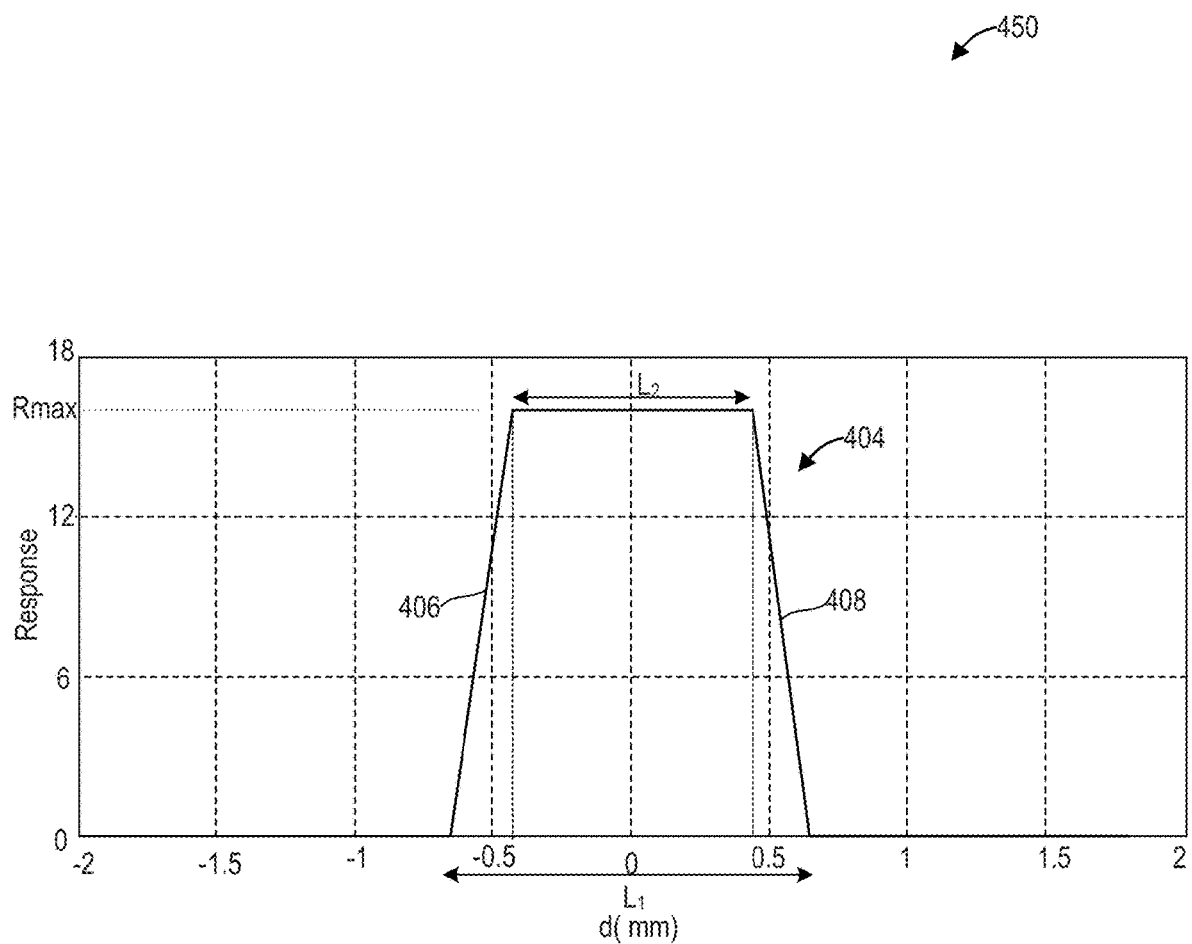
FIG. 4B shows a spatial domain response of a detector of the imaging system with the post-patient collimator of FIG. 3B having the anti-aliasing shape, according to an embodiment of the invention.
Figure 5:
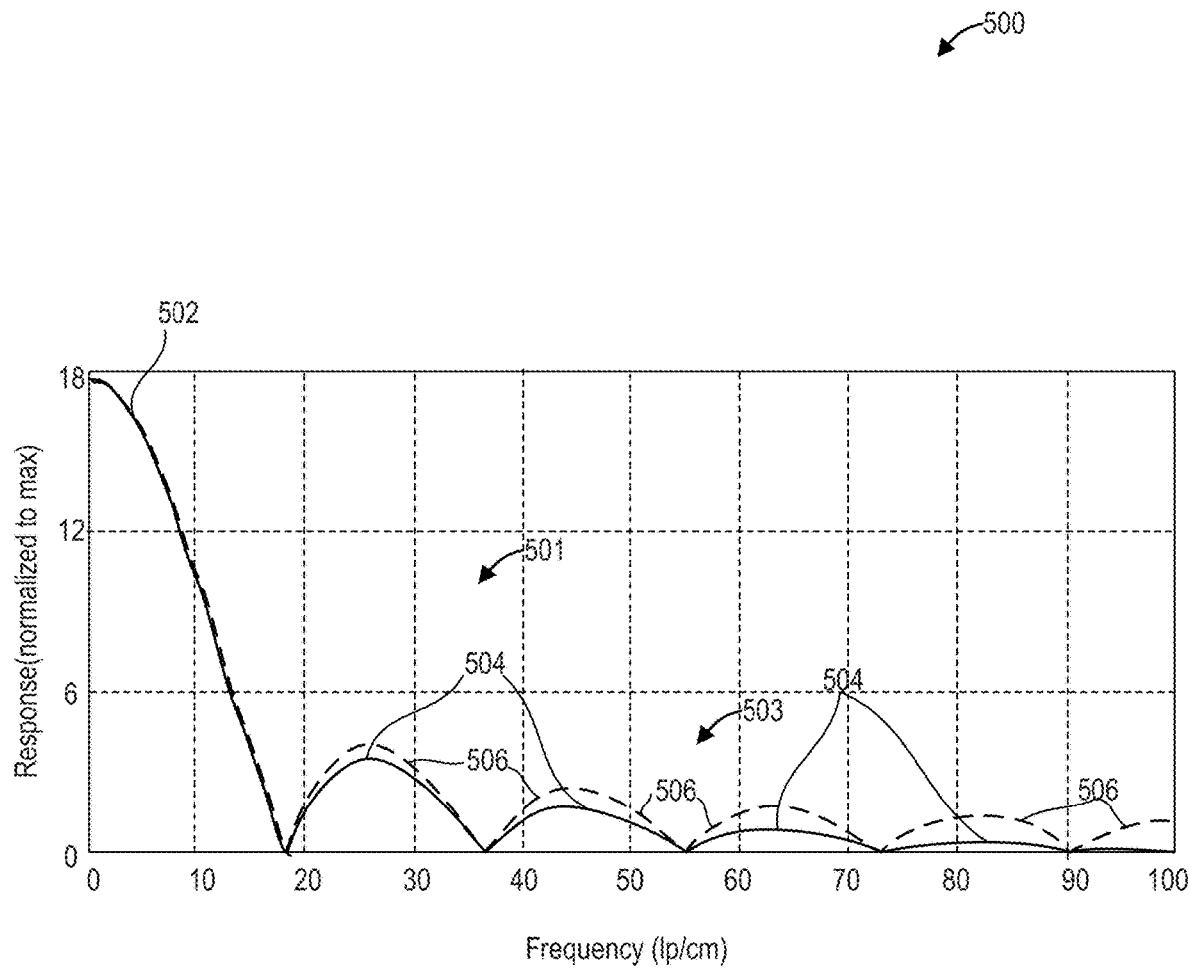
FIG. 5 shows a frequency domain response of the detector of the imaging system, according to an embodiment of the invention.
Figure 7:
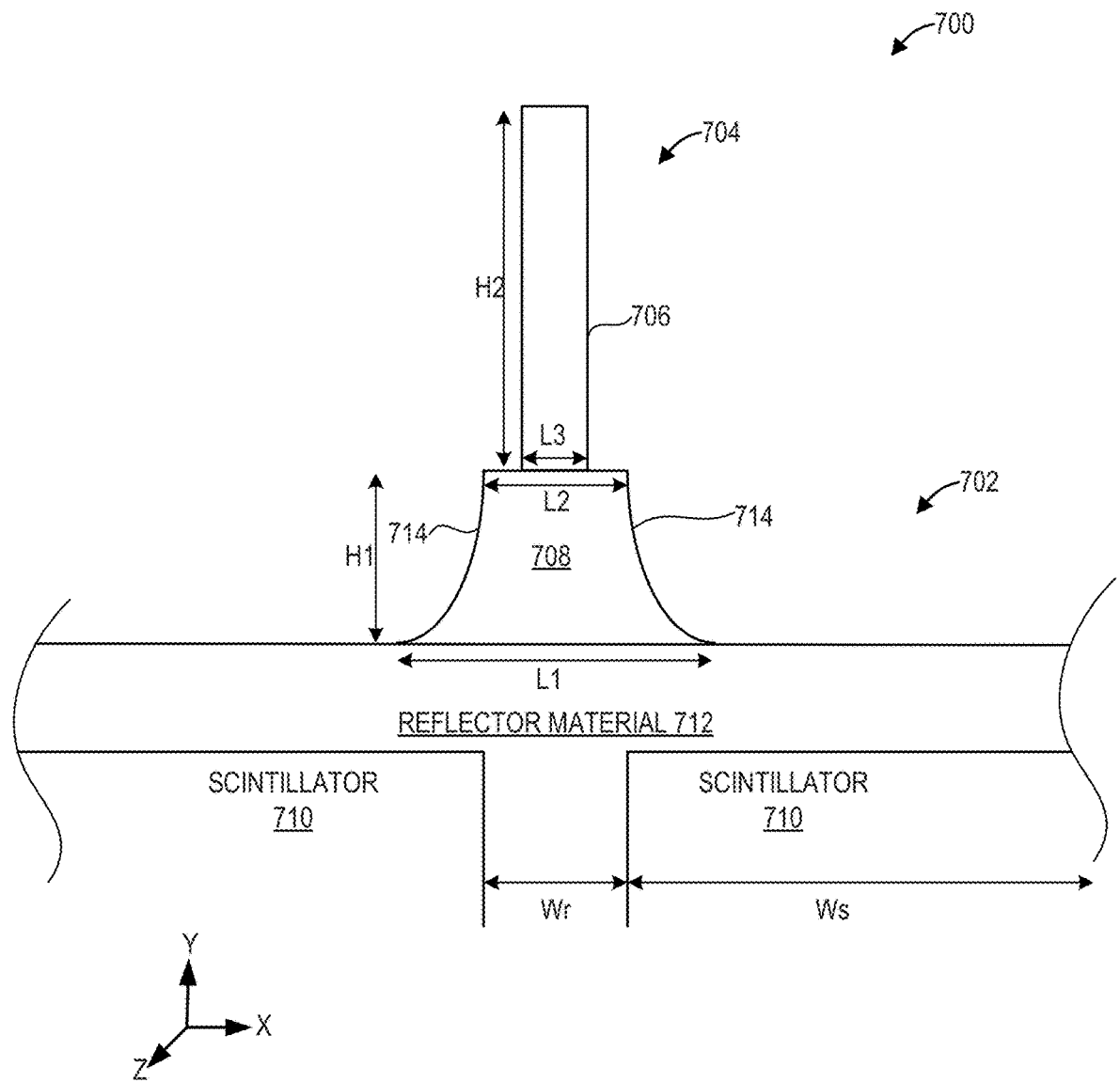
FIG. 7 shows a collimator plate having an anti-aliasing shape, according to an embodiment of the invention.
Figure 8A:
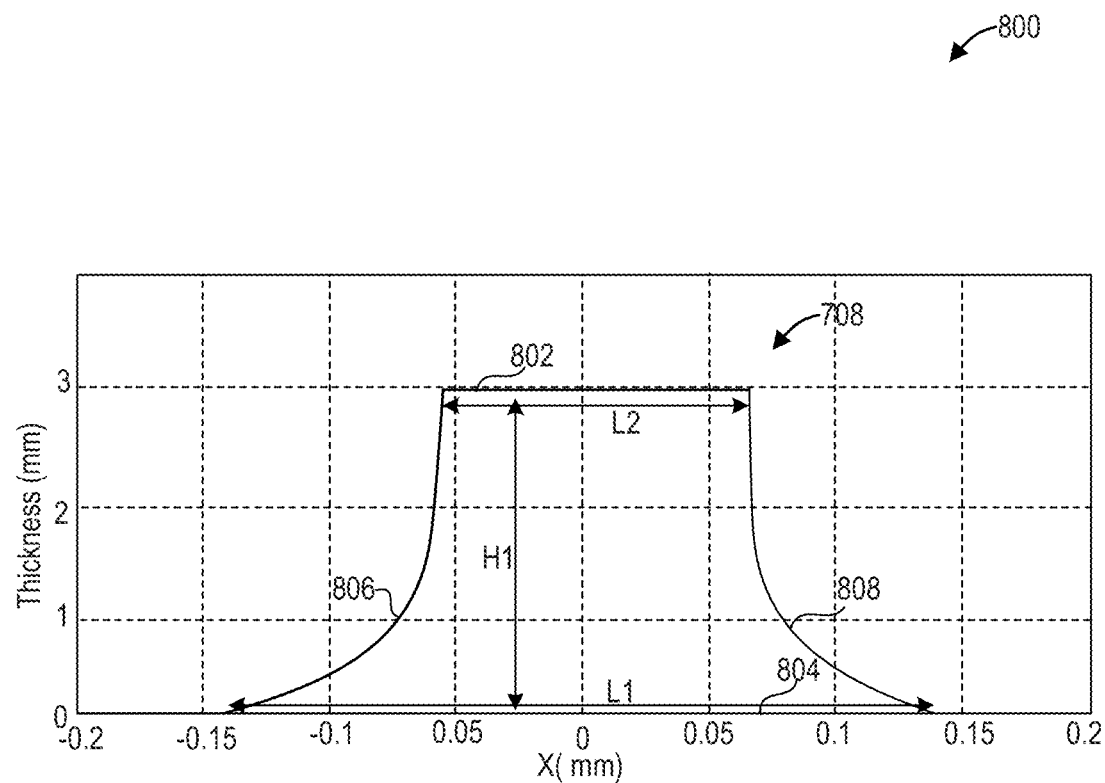
FIG. 8A shows a magnified view of the collimator plate, according to an embodiment of the invention.
Figure 8B:
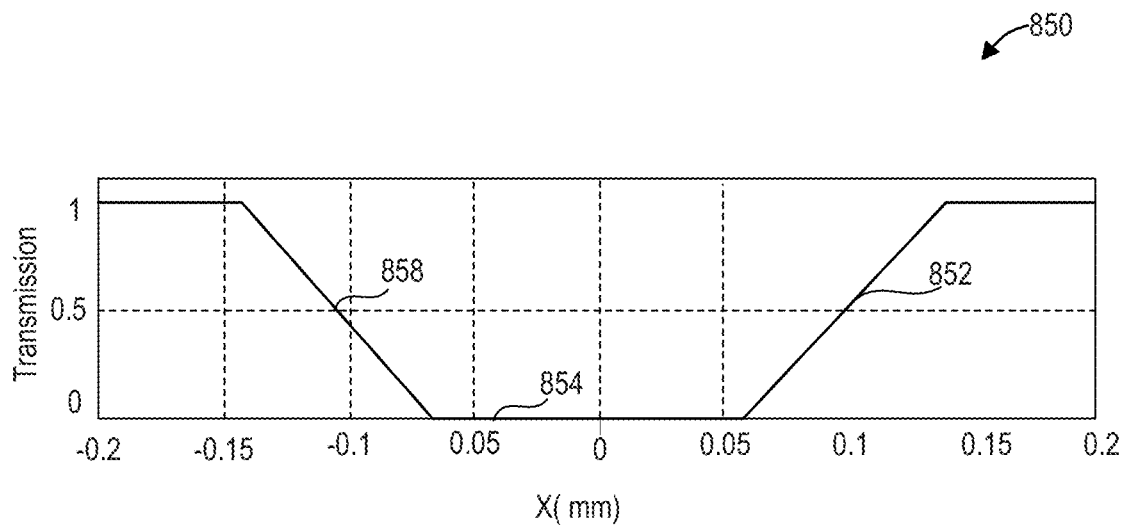
FIG. 8B shows a transmission profile of the collimator plate, according to an embodiment of the invention.
Figure 9:
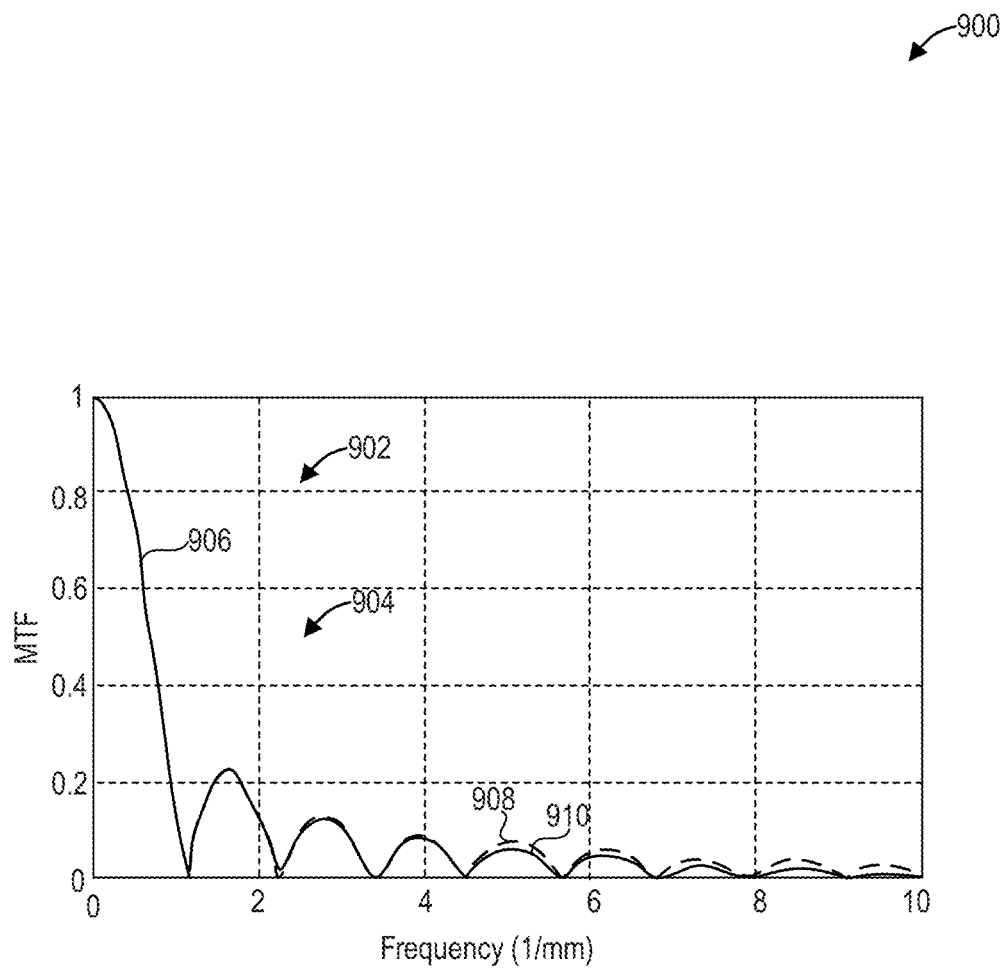
FIG. 9 shows a modulation transfer function of the detector having the collimator plate, according to an embodiment of the invention.
Figure 10:
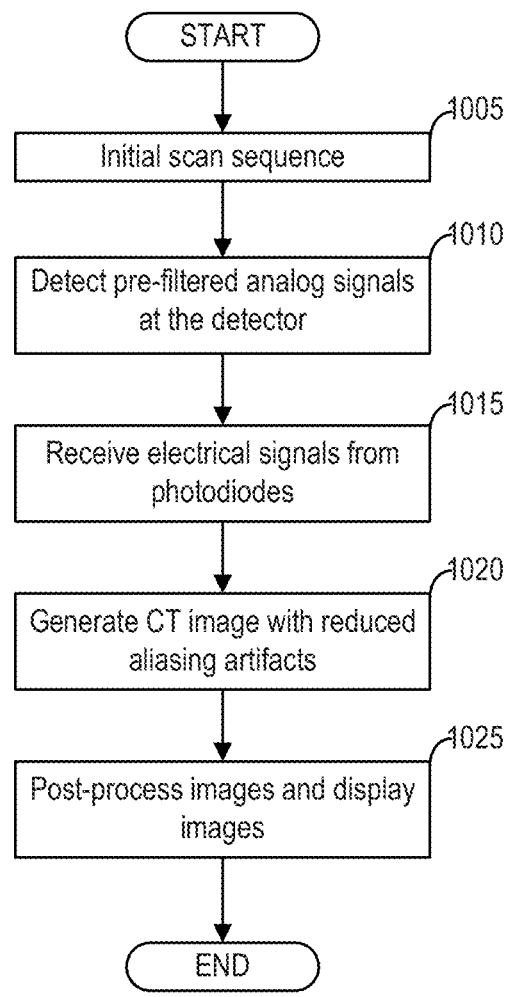
FIG. 10 shows a high-level flow chart illustrating an example method for reducing aliasing artifacts in the imaging system using collimators having smoother transition profiles.

According to embodiments disclosed herein, the shape of the post-patient collimator may be adjusted so that the aliasing artifacts may be reduced in order to generate a smoother transition profile. The smoother transition profiles lead to a reduction in the higher frequency signals that otherwise wrap around and generate the aliasing artifacts in the images. In one example, the post-patient collimator may include bell-shaped regions, as shown in FIG. 3B. A spatial domain response of the detector of the imaging system with the post-patient collimator having a bell-shaped structure is shown in FIG. 4B, and as such, this results in a reduced aliasing effect, as observed in the detector frequency response curve (FIG. 5). In another example, the anti-aliasing shape may be incorporated in a collimator plate coupled to the detector as shown in FIG. 7. An exploded view of the collimator plate is shown in FIG. 8A and a transmission profile of the collimator plate is shown in FIG. 8B. A modulated transfer function (MTF) of the detector (FIG. 9) shows a reduction in the higher frequency components detected by the detector when the anti-aliasing collimator plate is used. A method for reducing aliasing artifacts by pre-filtering the signals using the anti-aliasing shape of the collimator is shown in FIG. 10. It may be appreciated that the pre-filtering is performed in the analog domain, before the data is digitized. In this way, the anti-aliasing collimator may serve as analog pre-filter that reduces aliasing artifacts without performing adjustments such as adjusting a focal spot of the source or adjusting a shape of the detector cell, for example.

Though a CT system is described by way of example, it should be understood that the present techniques may also be useful when applied to images acquired using other imaging modalities, such as tomosynthesis, and so forth. The present discussion of a CT imaging modality is provided merely as an example of one suitable imaging modality. Other imaging modalities that may be use the present techniques include diagnostic radiography, tomosynthesis, cone beam CT, and other modalities that utilize collimators. Further, the principles described herein may also apply to ultrasound if the "collimator" is used to attenuate sound.

Figure 1:
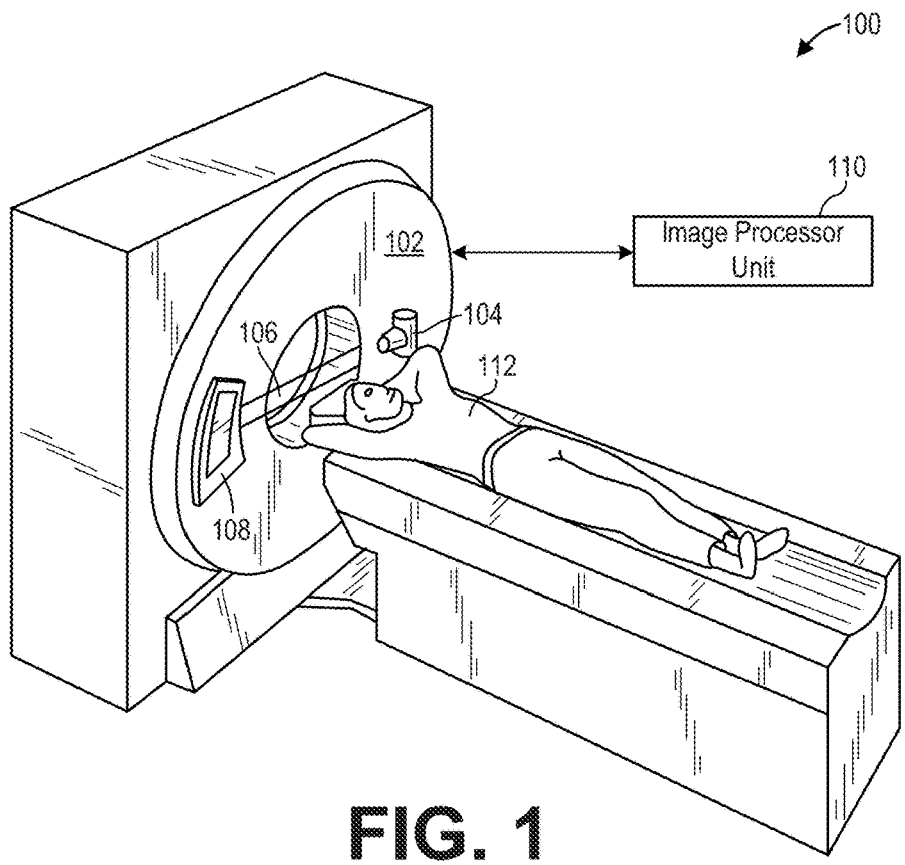
FIG. 1 shows a pictorial view of an imaging system according to an embodiment of the invention.
Figure 2:
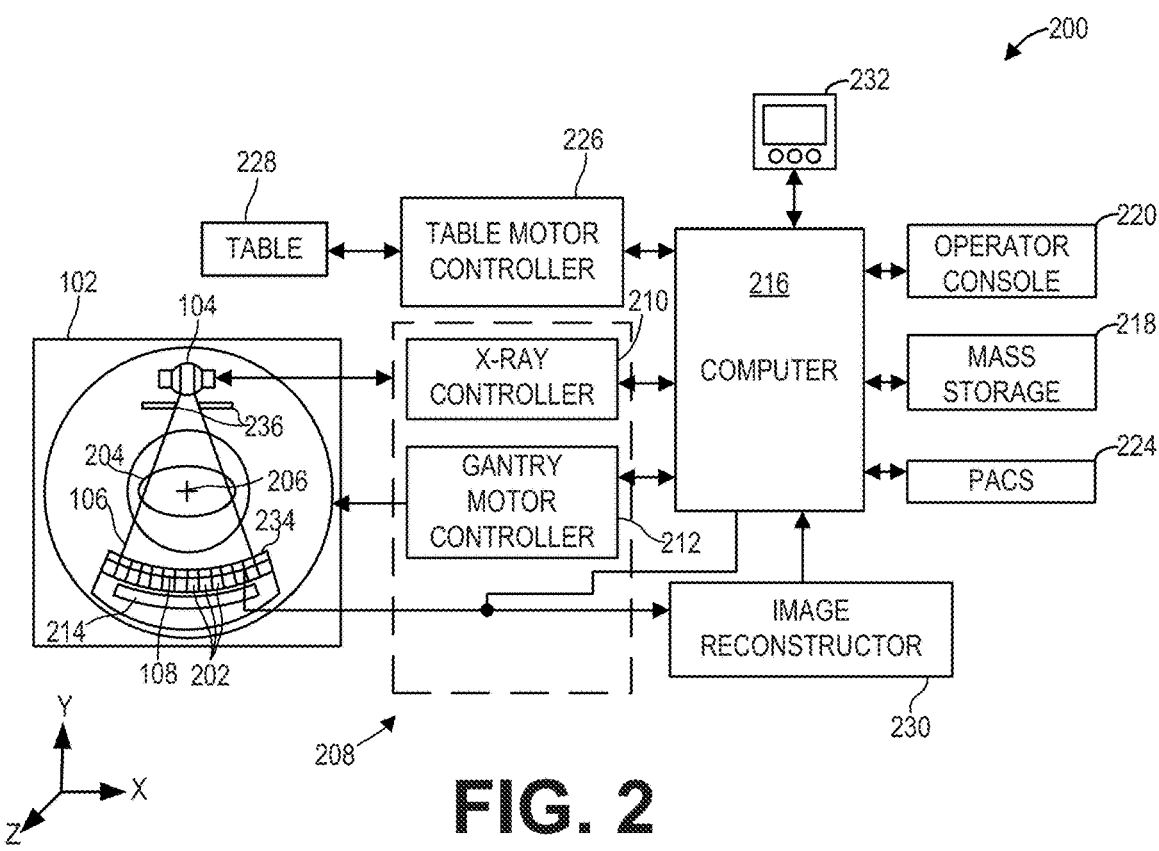
FIG. 2 shows a block schematic diagram of an exemplary imaging system including a post-patient collimator, according to an embodiment of the invention.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

FIG. 2 illustrates an exemplary imaging system 200 similar to the CT system 100 of FIG. 1. In one embodiment, the system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data. FIG. 2 includes a Cartesian coordinate system, and the detector elements 202 extend in row along the x axis. It is to be understood that additional rows of detector elements may extend along the z axis.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

In certain embodiments, the system 200 may include a pre-patient collimator plate 236 positioned in between the x-ray radiation source 104 and the subject or patient 204 for reducing patient x-ray dose during a scan with the system 200. The pre-patient collimator plate 236 includes an aperture that shapes the x-ray beam 106 reaching the subject 204 by adjusting a width of the beam leaving the x-ray tube, for example. Herein, by adjusting the aperture width, the width of the beam may be adjusted. The pre-patient collimator plate 236 adjusts the width of the beam to match the size of the detector array 108 so that any unnecessary patient dose is reduced.

X-ray radiation that impinges on the subject 204 is attenuated as it traverses the subject 204. The radiation that traverses the subject 204 is detected by one or more pixels, or channels of the detector array 108 and a signal is generated that is indicative of characteristics of the radiation that is detected by the pixel. A CT image may be reconstructed from the signal. In addition, some of the radiation impinging on the subject 204 may be scattered (e.g., due to interactions with the subject 206). While the unscattered attenuated radiation is referred to as primary radiation, the scattered radiation is referred to as secondary radiation. As such, the secondary radiation that is detected by the one or more pixels of the detector array 108 may increases noise and further reduce the quality of the CT image produced based upon the detector signal.

In order to reduce the scattered or secondary radiation from being detected by the detector array 108, the system 200 may include an anti-scatter collimator or post-patient collimator 234 positioned between the subject 204 and the detector array 108. The post-patient collimator 234 is configured to allow the primary radiation to pass through the collimator to be detected by the pixel of the detector array 108. In addition, the post-patient collimator 234 blocks the scattered radiation from reaching the detector array 108. As such, the post-patient collimator 234 may absorb the scattered radiation thereby shielding the detector array 108 from the scattered radiation, and thus reducing noise in the pixels of the detector array 108, as shown below. The post-patient collimator may include a plurality of collimating elements (also referred to as high-attenuating regions) that extend in a row along the x axis with the detector elements 202. Further, while not visible in FIG. 2, each collimator element may extend along an entirety of the detector array in the z axis. In other examples, the plurality of collimator elements may be arranged in multiple rows and thus multiple collimator elements may extend along the z axis.

Turning now to FIG. 3A, a magnified view 300 of a portion of a post-patient collimator or anti-scatter collimator 302 is shown. The post-patient collimator 302 is one non-limiting example of the post-patient collimator 234 shown in FIG. 2. As described previously, the post-patient collimator 302 is positioned between a source side 312 and a detector side 314 and is used to collimate the attenuated signals arising from a subject placed in the source side 312 towards the detector side 314. Herein, the source side 312 may include a source (such as the source 104 of FIGS. 1 and 2), a pre-patient collimator (such as the pre-patient collimator 236 of FIG. 2), and a subject (such as the subject 204 of FIG. 2). The detector side 314 may include a detector array (such as the detector array 108 of FIGS. 1 and 2). Specifically, the post-patient collimator 302 is placed in front of the detector array to absorb the scattered radiation and allow the primary radiation to pass through the post-patient collimator 302 to the detector side 314.

The post-patient collimator 302 may include high attenuating plates or regions 306 composed of materials such as tungsten or lead, alternating with low attenuating plates or regions 308. The high attenuating regions 306 may attenuate the scattered radiation to a higher degree that the low attenuating regions 308. Together, the high attenuating regions 306 and the low attenuating region 308 may form a grid-like pattern. FIG. 3A includes the Cartesian coordinate system, showing that the high attenuating regions 306 are spaced along the x axis, similar to the detector elements (not shown in FIG. 3A). Each high attenuating region 306 may extend along the z axis a suitable distance (e.g., the entirety of the detector array). FIG. 3A may be a side view of the collimator (e.g., a head-on view while looking down the bore of the CT gantry). In other examples, FIG. 3A may be a cross-sectional view taken along the length of the collimator at a suitable plane of the z axis.

In some examples, the regions 308 may not be composed of any material (e.g., may be void of material), so air filling the regions 308 between the regions 306 may allow the radiation to pass through without any attenuation. As such, the high attenuation regions may absorb radiation scattered from the subject, whereas the low attenuation regions may allow the primary radiation passing through the subject to transmit through to channels (or pixels) of the detector (as indicated by arrows 310). Said another way, the high attenuation regions allow a lower percentage of scattered radiation to pass through by blocking a major portion of the scattered radiation, and the low attenuation regions allow a higher percentage of the primary radiation to pass through. In some example, the high attenuation regions 306 block 90% of the scattered radiation, and the low attenuation regions 308 may transmit 99.9% of the primary radiation arising from the object to reach the active regions of the detector.

The high attenuation regions 306 typically have a rectangular shape of uniform height, h (along the y axis) and uniform width, w (along the x axis). Each high attenuation region 306 is separated from an adjacent high attenuation region 306 by a space or gap, d. As such, the space d between adjacent high attenuation regions may correspond to the width of the low attenuation regions 308, for example.

The space d between each adjacent high attenuation regions 306 is uniform and may be sized to match each channel or pixel of the detector, for example. In some embodiments, the space d may be sized to match a width W (or surface area) of the channel of the detector. Specifically, the width W of the channel represents an active region of the detector where x-ray radiation is captured, and the space d may be adjusted to match the width of the active region of the detector. Herein, the width w of the high attenuation regions 306 may be sized to match the inactive (or dead space or dead zone) of each channel of the detector. For example, each detector includes a plurality of channels including an active region and an inactive region. Radiation detected in the active region of the channel is used for creating the CT images, while radiation falling on the inactive region of the channel is not detected by the detector. In some examples, a transverse dimension of the active region may be between 0.5 mm to 1.5 mm, and the transverse dimension of the inactive region may be between 0.2 mm to 0.3 mm. By aligning the high attenuation regions 306 with the inactive regions of the channel and the low attenuating regions 308 with the active regions of the channel, scattered radiation may be blocked while the primary radiation may be allowed to pass through to the active regions of the channel.

The rectangular shape of the high attenuation region 306 may give rise to a rectangular transition profile of the post-patient collimator 302, which in turn leads to a response of the detector having a rectangular profile, as shown in FIG. 4. The post-patient collimator 302 having a rectangular transition profile may henceforth be referred to as a rectangular post-patient collimator.

Figure 4A:
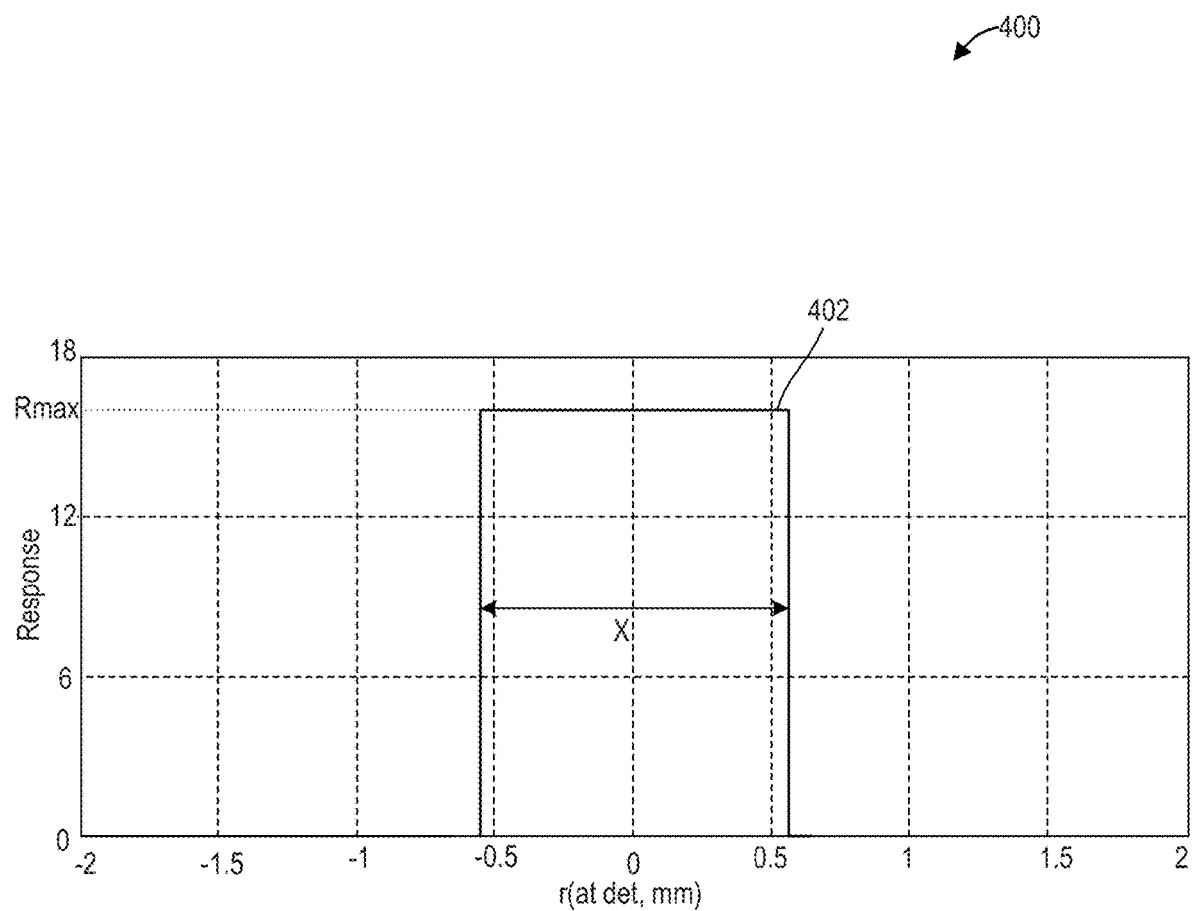
FIG. 4A shows a spatial domain response of a detector of the imaging system with the post-patient collimator of FIG. 3A, according to an embodiment of the invention.

Turning now to FIG. 4A, graph 400 shows a response of a detector when a rectangular post-patient collimator (such as the rectangular post-patient collimator 302 of FIG. 3) is placed in front of the detector. The x-axis of graph 400 represents a transverse distance across a channel of the detector and the y-axis represents a spatial domain response of the detector. The spatial domain response of the detector is a measure of an amount of radiation detected across a spatial region formed by a channel of the detector.

When the rectangular post-patient collimator as described with reference to FIG. 3A is aligned with individual channels (specifically, individual active regions of the detector, for example) of the detector, the x-ray beam may be able to transmit only through the low attenuation regions 308 of the collimator and be detected by the channels of the detector. Thus, the response of the detector channel may include a rectangular shape as shown by response 402 in graph 400. Herein, the width of the response 402 may be equal to the space d between adjacent high attenuation regions. Specifically, the width of the response 402 may be equal to the width of the low attenuation region 308 shown in FIG. 3A.

The y-axis of response 402 represents the spatial domain response of the detector. For example, the spatial domain response of the detector is a measure of a sum total radiation detected by all the channels of the detector. For example, the spatial domain response (R) of the detector may be mathematically represented by equation (1) as shown below:

$$R = \Sigma_{k=0}^{n} R_k \quad (1)$$

where $R_k$ is the response of $k^{th}$ channel of the detector. Herein, the detector includes n number of channels and $R_k$ is a measure of the amount of radiation detected by the kth channel.

Mathematically, the rectangular response R of the detector may be represented in 1-D by equation (2), as shown below:

$$R(r) = \begin{cases} R\max, & |r| < \dfrac{X}{2}, \\ 0, & |r| \geq \dfrac{X}{2}. \end{cases} \quad (2)$$

where Rmax is the maximum response of the detector, r is the distance along the detector, and X is equal to the width of the detector (or rectangular function).

In the example detector response shown in graph 400, R(x)=0 when r≥0.55 and R(x)=Rmax when |r|<0.55. Thus, the detector detects a maximum amount of primary radiation in the region between −0.55 mm and +0.55 mm. Herein, the width of the response is equal to 1.10 mm. A sharp transition occurs at the boundaries occurring at −0.55 mm and +0.55 mm. For example, all of the radiation is blocked at r<−0.55, and the response R=0, however, at r=−0.55, the response R quickly reaches Rmax, indicating that a maximum amount of radiation is getting through to the detector. Likewise, another sharp transition occurs at r=0.55. These sharp transitions may lead to high frequency side lobes in the frequency domain as shown below.

For a rectangular spatial domain response of the detector as shown by response 402, a corresponding frequency domain response may be computed by performing a 1-D Fourier Transform of the spatial domain response. The Fourier Transform is a signal processing tool which is used to decompose a signal into its sine and cosine components. The output of the transformation represents the signal in the Fourier or frequency domain, while the input image is the spatial domain equivalent. In the Fourier domain image, each point represents a particular frequency contained in the spatial domain image. Mathematically, the frequency domain response may be represented by equation (3) as shown below:

$$R(u) = \int_{-\infty}^{\infty} R(r) e^{-j2\pi u r} dr = X\mathrm{sinc}(\pi X u) \quad (3)$$

The graphical representation of the sinc function is shown in graph 500 of FIG. 5. Turning to FIG. 5, a frequency domain response 501 includes a central frequency response 502 (shown as dashed line), and additional higher frequency components 504 (dashed lines). The frequency response 502 of the detector represents the signal that is used to generate an image of the object that is being scanned. However, the higher frequency components 504 contribute to noise in the imaging system. Herein, the high frequency components 504 are generated because of the sharp transition occurring at the boundary of the rectangular response function, for example. As such, these high frequency components 504 may wrap around and cause image artifacts, as shown in FIG. 6.

Figure 6:
FIG. 6 shows an example CT image with aliasing artifacts, according to an embodiment of the invention.

Turning now to FIG. 6, image 600 shows an example CT image of an anatomy of a subject (such as the subject 204 of FIG. 2) scanned in an imaging system (such as the imaging system 200 of FIG. 2). Herein, the CT image is reconstructed using frequencies detected by a detector of the imaging system. When rectangular post-patient collimators are used in the imaging system, high frequency components are generated. High frequency components of frequency signals detected by a detector may wrap around and cause streaky or bandy artifacts as indicated by arrows 604 in the image 600. Such artifacts, called aliasing or wrap around artifacts, interfere with a clinician's ability to read the image 600.

To combat aliasing, one or more anti-aliasing methods such as quarter detector offset, focal spot wobble, and comb filtering may be used. Typically, over sampling may reduce aliasing artifacts in the CT image. In quarter detector offset method, the detector center is offset by a quarter of the detector cell width with respect to the iso-center of the detector. As a result, when the gantry rotates 180°, each sample is interleaved with a previously acquired sample, thus increasing the sampling by a factor of two. Thus, such an arrangement results in double sampling and reduces aliasing. Further, the quarter detector offset may result in a detector that is no longer symmetric, potentially wasting detector space.

In focal spot wobble method, the focal spot of the x-ray beams may be intentionally shifted or switched or wobbled between two or more optimal focal spot locations during a scan or between scans, thereby at least doubling the sampling in the system. However, additional components may be integrated in the x-ray tube to deflect (either electrostatically or electromagnetically) the focal spot of the x-ray beam. Deflecting the focal spot to two locations, for example, requires doubling the sampling rate to keep the same number of views per rotation. This increase in sampling rate reduces the amount of signal in each acquisition, potentially increasing noise and low signal artifacts.

In comb filtering method, a diaphragm is inserted in front of the detector to reduce an aperture of the detector to increase the spatial resolution of the detector. Herein, the diaphragm reduces the aperture opening of each pixel of the detector, which changes a modulation transfer function of the detector to higher frequencies wherein the modulation transfer function is a spatial frequency response of the detector. As such, the reduction in aperture increases the amount of aliasing, which may be reduced by oversampling with multiple focal spot positions or focal spot wobble as previously described. However, in such systems, the dose efficiency of the detector may be reduced. The dose efficiency is a measure of the amount of x-rays that are needed to produce an image of desirable/suitable quality, relative to an ideal detector. If the dose efficiency decreases, a higher amount of x-rays may be needed to produce the image with the desired quality, causing increased radiation dose for the patient. Adding the hardware to enable this feature may be difficult to manufacture and may be expensive.

The inventors have recognized that it may be possible to reduce aliasing in the CT images without using additional measures such as focal spot wobble, for example. Herein, the proposed method includes analog pre-filtering of the signals passing through the subject by utilizing a non-rectangular post-patient collimator as shown in FIG. 3B.

Turning now to FIG. 3B, a magnified view 350 of a portion of a post-patient collimator 352 is shown. It may be appreciated that the post-patient collimator 352 may extend in two dimensions and may be aligned with respect to a detector array (such as detector array 108 of FIGS. 1 and 2). The post-patient collimator 352 may be a non-limiting example of the post-patient collimator 234 shown in FIG. 2. FIG. 3B includes the Cartesian coordinate system, showing that the high attenuating regions 360 are spaced along the x axis, similar to the detector elements (not shown in FIG. 3A). Each high attenuating region 360 may extend along the z axis a suitable distance (e.g., the entirety of the detector array). FIG. 3B may be a side view of the collimator (e.g., a head-on view while looking down the bore of the CT gantry). In other examples, FIG. 3B may be a cross-sectional view taken along the length of the collimator at a suitable plane of the z axis.

The post-patient collimator 352 may include a shape that reduces aliasing artifacts. Specifically, the shape of the post-patient collimator 352 may include an anti-aliasing shape so that the transition profile does not include a sharp transition (as described with reference to FIGS. 3A and 4A). Herein, the anti-aliasing shape of the post-patient collimator 352 results in a smoother or tapered transition profile as described below. Hereafter, the post-patient collimator 352 may be referred to as an anti-aliasing post-patient collimator.

Similar to the rectangular post-patient collimator 302 of FIG. 3A, the anti-aliasing post-patient collimator 352 may include a plurality of high attenuation regions 360 interleaved with a plurality of low attenuation regions 362. Each high attenuating region 360 may include a non-uniform transition profile and may further be aligned with a respective inactive region of a respective channel of a detector of the medical imaging system as described below. In contrast to the rectangular post-patient collimator 302, the anti-aliasing post-patient collimator includes a non-rectangular shape that reduces aliasing. Some non-limiting examples of the anti-aliasing shape of the collimator include a sinusoidal shape, a curved shape, a dome or bell shape, an apse, a rounded-trapezoidal shape, a rounded-pyramidal shape, and the like. Herein, the rounded-trapezoidal shape includes a trapezoid with rounded edges and the rounded-pyramidal shape includes a pyramid with rounded vertex, for example. Additional shapes include designs based on Gaussian profiles or the spatial response of known anti-aliasing filters, either analog or digital, such as the Kaiser window filter. Each high-attenuating region may extend non-uniformly along at least one axis. As shown the high-attenuating regions extend non-uniformly along the y axis and along the x axis. Each high-attenuating region extend uniformly along the z axis in some examples. In other examples, each high-attenuating region may extend non-uniformly along the z axis (e.g., the front and/or back face of each high-attenuating region may be curved).

Similar to the rectangular post-patient collimator 302, the anti-aliasing post-patient collimator 352 is positioned between a source side 356 and a detector side 358 and is used to collimate the attenuated signals arising from the subject towards the detector side 358. Herein, the source side 356 may include a source (such as the source 104 of FIGS. 1 and 2), a pre-patient collimator (such as the pre-patient collimator 236 of FIG. 2), and a subject (such as the subject 204 of FIG. 2). The detector side 358 may include a detector array (such as the detector array 108 of FIGS. 1 and 2). Specifically, the anti-aliasing post-patient collimator 352 is placed in front of the detector array to absorb the scattered radiation and additionally modulate or shape the primary radiation passing through the anti-aliasing post-patient collimator 352 as described below. Said another way, the anti-aliasing post-patient collimator may lead to a non-uniform attenuation of the signals reaching the pixels of the detector.

Similar to the rectangular post-patient collimator 302 of FIG. 3A, the anti-aliasing post-patient collimator 352 includes a plurality of high attenuation regions 360 composed of materials attenuating the radiation by a higher degree, such as tungsten or lead, alternating with a plurality of low attenuating regions 362 composed of materials attenuating the radiation to a lower degree. Together, the pluralities of regions 360 and 362 form a grid-like pattern. In some example, the plurality of regions 362 may not be composed of any material (e.g., filled with air), thus allowing the radiation to pass them through without any attenuation. In such an example, each high attenuation region 360 may be separated from an adjacent high attenuation region by a gap.

Similar to the rectangular post-collimator 302, the high attenuation regions 360 of the anti-aliasing post-patient collimator 352 may absorb radiation scattered from the subject, while the low attenuation regions 362 of the anti-aliasing collimator 352 may allow the primary radiation passing through the subject to transmit through to channels (or pixels) of the detector (as indicated by arrows 364). Thus, the high attenuation regions allow a lower percentage of scattered radiation to pass through by blocking a major portion of the scattered radiation, and the low attenuation regions allow a higher percentage of the primary radiation to pass through. In contrast to the rectangular post-patient collimator 302, the anti-aliasing post-patient collimator 352 may additionally shape or modulate the primary radiation based on a shape of the anti-aliasing post-patient collimator as discussed below. In one example, the anti-aliasing post-patient collimator may modulate the signals in a non-uniform manner, resulting in a reduction in aliasing artifacts as explained below.

Specifically, in contrast to the sharp transition profile of the high attenuation region 306 of the rectangular post-patient collimator 302, the high attenuation region 360 of the anti-aliasing post-patient collimator 352 may include a smoother or gradient transition profile. For example, sides 366 of the high attenuation region have a sinewave-like or a distorted sinewave-like profile or bell-shape profile. Herein, the transition from point A to point C of the high attenuation region 360 of the anti-aliasing post-patient collimator 352 is gradient and not sharp. Likewise, the transition from point C to point B of the anti-aliasing post-patient collimator 352 is also gradient. Together, curves AC and CB form the transition profile of the high attenuation region 360 of the anti-aliasing post-patient collimator 352.

Unlike the rectangular post-patient collimator 302, the width w of the high attenuation regions 360 of the anti-aliasing post-patient collimator 352 is not uniform. A bottom portion of the high attenuation region 360 may have a larger width compared to a top portion of the high attenuation region. The bottom portion of the high attenuation region 360 may correspond to the region that is closer to the detector side while the top portion of the high attenuation region 360 may correspond to the region closer to the source side of the imaging system. Thus, the width of the high attenuation region 360 of the anti-aliasing post-patient collimator 352 increases as the distance of the collimator to the detector decreases. In other words, the bottom most portion of the high attenuation region 360 has the maximum width (e.g., $AB = w_{max}$), and the topmost portion of the high attenuation region 360 has the minimum width, $w_{min}$. Thus, the width of the high attenuation region 360 is not uniform and further varies along the y-axis.

In some examples, the maximum width $w_{max}$ may be larger than a width of the inactive region ($W_{inactive}$) of a detector channel such that the high attenuation region may partially overlap into the active region of the detector channel. An extent of overlap may be based on a shape of the of the high attenuation region of the anti-aliasing post-patient collimator, for example. The collimator length (in the y direction) over the inactive region may vary, but anti-aliasing benefits may only be realized when the collimator length is varying over the active region of the detector. Varying the collimator length over the inactive area may provide benefits if the collimator gets misaligned, for example.

In addition, a height h1 of the high attenuation region 360 of the anti-aliasing post-patient collimator 352 is not uniform. Herein, the height h1 varies along the x-axis. At point A, the height of the high attenuation region 360 is zero. Then, the height of the high attenuation region 360 gradually increases along the x-axis, reaching a maximum height, H1, at point C, thereafter decreases continually along the curve CB, and finally becomes zero at point B. In this way, the high attenuation region 360 includes a smoother transition profile.

Similar to the high attenuation region 360, the low attenuation region 362 may include a height h2 that is not uniform. The height h2 varies along the x-axis. At point C, the height of the low attenuating region 362 is zero. The height h2 gradually increases along the x-axis from point C, reaching a maximum height H2 at point B. Between points B and E, the height of the low attenuating regions remains maximum at H2. From point E to point F, the height h2 of the low attenuating region 362 continues to decrease, and finally reaches zero at point F. In this way, the low attenuation region 362 includes a smoother transition profile.

Consider an example configuration wherein the low attenuation regions are void of materials. In such an example, adjacent high attenuation regions 360 of the anti-aliasing post-patient collimator 352 are separated by a gap or space, d(y). Unlike the space d between adjacent high attenuation regions of the rectangular post-patient collimator 302, the gap d(y) between adjacent high attenuation regions of the anti-aliasing post-patient collimator 352 is not uniform. The gap d(y) between adjacent high attenuation regions may correspond to the width of the low attenuation regions 362, for example. Thus, the width of the low attenuation regions 362 of the anti-aliasing post-patient collimator 352 is also non-uniform.

The gap d(y) (or width) of the low attenuation regions 362 is larger at or near the detector side 358, while the gap d(y) is smaller towards the source side 356 of the imaging system. More specifically, the gap d(y) between points B and E is smaller than the gap d(y) between points C and F in view 350. Thus, the gap d(y) varies from a minimum $d_{min}$ to a maximum $d_{max}$ when moving along the y-axis from the detector side 358 to the source side 356 of the imaging system. In some examples, $d_{min}$ may be smaller than a width of the active region of the detector channel.

Thus, the varying gap between adjacent high attenuation regions and the varying width of the high attenuation regions of the anti-aliasing post-patient collimator 352 results the post-patient collimator 352 having a varying area. In some examples, the low attenuation regions 362 may have an inverted shape of the high attenuation regions 360. In the view 350, the high attenuation region 360 may include a dome or bell shape, and the low attenuation region 362 may include an inverted dome or bell or cup shape, for example. Together, the high and the low attenuation regions of the anti-aliasing post-patient collimator 352 modulate the primary radiation as indicated by arrows 364. By varying the gap, a pixel aperture may be modulated. This "apodization" may result in non-uniform attenuation of the primary radiation.

For illustrative purposes, a length of each arrow 364 represents a level or amount of primary radiation, assuming no patient attenuation for this example, passing through the anti-aliasing post-patient collimator 352 and reaching the detector (e.g., an active region of the detector). Herein, the width of the active region may be $W_{active}$. In some examples, $W_{active}$ may be larger than $W_{inactive}$. In some other examples, $W_{active}$ may be equal to $W_{inactive}$. For example, a smaller length of the arrow 364 indicates a lower amount of the primary radiation that is transmitted to the detector channel. A larger length of the arrow 364 indicates a higher amount of primary radiation that is transmitted to the detector channel. Herein, an amount of primary radiation passing through the high attenuation region 360 may increase with decreasing height (and increasing width) of the high attenuation regions. Said another way, the amount of attenuation of the signals by the region 360 is proportional to the height h1 of the region 360 (or the amount of transmission is inversely proportional to the height of the region 306). In addition, the level of transmission of the signals through the low attenuation region is directly proportional to the height h2 of the low attenuation region. Thus, the central regions of the high attenuation regions 360 block a higher percentage of the primary radiation than the ends or edges of the high attenuation regions 360. In other words, some of the primary radiation incident along the ends of the high attenuation regions leaks into the detector channel. In this way, the post-patient collimator 352 may filter the incoming primary radiation. It may be appreciated that the incoming primary radiation is attenuated by the object placed in the imaging system. Herein the non-uniform profile of the anti-aliasing post-patient collimator is non-uniform across an entire cross-section area of the high attenuating region and is also non-uniform across an entire cross-section area of the low-attenuating region. In this way, the transmission of the signal (e.g., radiation) may be non-uniform across the entire cross-sectional area of the high-attenuating region and may be non-uniform across the entire cross-sectional area of the low-attenuating region, even if the regions re shaped with portions that attenuate uniformly. For example, it may be noted that there may be some regions in the low attenuation region (e.g., between points B and E in view 350) where the transmission of the primary radiation may be uniform.

Thus, by incorporating the anti-aliasing shape to the post-patient collimator, the signals undergo an analog pre-filtration in the spatial domain. Herein, by pre-filtering (e.g., filtering performed before signals reach the detector) the signals in the spatial domain, higher frequency components that would otherwise wrap around and generate aliasing artifacts in the image may be reduced, as described below.

The smoother transition profile of the anti-aliasing post-patient collimator 352 may be achieved by using any non-rectangular overall shape. Some examples of non-rectangular shapes include bell shape, dome shape, sinusoidal shape, and the like. Some more examples of such non-rectangular shapes include trapezoidal shape, pyramidal shape, and the like. The edges in these shapes may be additionally rounded to reduce sharp transitions for the signals. In some examples, a level of attenuation of signals by the plurality of high attenuating regions may be based on the shape of the high attenuation regions. Additionally, a level of transmission of signals by the low attenuating regions may be based on the shape of the high attenuation regions. Further, in some examples an overall non-rectangular shape may be achieved by a plurality of high-attenuating areas that are shaped together to form the non-rectangular shape, where the high-attenuating areas themselves are rectangular, such as a plurality of small rectangles that collectively form a non-rectangular shape. In still further examples, the high-attenuating region may be comprised of materials with different attenuating properties, where a higher-attenuating material is formed in a non-rectangular shape surrounded by lower-attenuating material. In this way, the shape itself may be rectangular, but the attenuation may be non-rectangular. Additionally, an overall rectangular shape may be used if the collimator is rotated with respect to the detector array, such that a non-uniform transmission profile/response is still achieved.

Turning now to FIG. 4B, graph 450 shows a response of a detector when an anti-aliasing post-patient collimator (such as the anti-aliasing post-patient collimator 352 of FIG. 3B) is placed in front of the detector. The x-axis of graph 450 represents a transverse distance across a channel of the detector and the y-axis represents a spatial domain response of the detector.

When the anti-aliasing post-patient collimator as described with reference to FIG. 3B is aligned with individual channels or pixels (specifically, individual active regions of the detector, for example) of the detector, the x-ray beam may be able to transmit only through the low attenuation regions 360 of the collimator and be detected by the channels of the detector. Due to the non-uniform width of the low and high attenuation regions of the anti-aliasing post-patient collimator, the spatial domain response R of the detector may not include a rectangular shape. In one example, the spatial domain response R of the detector may include a trapezoidal shape as indicated by plot 404. Herein, the width of the response 404 may not be uniform.

Mathematically, the response R of the detector may be represented in 1-D by equation (4), as shown below:

$$R(x) = \begin{cases} R\max, & |d| < \frac{L2}{2} \\ 0, & |d| > \left(\frac{L2}{2} + \delta\right) \\ \left(\frac{L1}{2} - |d|\right) * \frac{R\max}{\delta}, & \text{else} \end{cases} \quad (4)$$

where Rmax is the maximum response of the detector, d is the distance along the detector, m is the slope of the sides of the response R, and $$\delta = \frac{L_1 - L_2}{2}.$$

Herein, $L_1$ represents the bottom length of the response R and $L_2$ represents the top length of the response R. Herein, the bottom length $L_1$ includes the length from when the responses begins to increase above zero to when the response again reaches zero and the top length $L_2$ includes the length where the response is equal Rmax In the example detector response shown in graph 450, $R(x)=0$ when $x \geq 0.6$ and $R(x)=R\max$ when $|x|<0.45$. Thus, the detector detects a maximum amount of primary radiation in the region between −0.45 mm and +0.45 mm. Herein, the maximum response Rmax occurs within 0.90 mm. In addition, the response $R(x)$ includes two linear transitions between the high and low response regions. Herein, the line 406 has a positive slope, while the line 408 includes a negative slope. The slope of the lines 406 and 408 may depend on an extent of overlap of the high attenuation region 360 with the active region of the detector channel, for example.

Similar to the rectangular response shown in FIG. 4A, a frequency domain response of the response 404 may be computed by performing a 1-D Fourier Transform of the spatial domain response. Thus, by using a non-rectangular shape of the post-patient collimator, the sampling on the detector may also be non-rectangular. The non-rectangular shape of the detector serves as an analog pre-filter to the spatial signal on the detector. This pre-filtering of the signal reduces higher frequency signals that would otherwise wraparound as aliasing as shown in FIG. 5.

Turning now to FIG. 5, graph 500 shows a frequency domain response 503 of the non-rectangular response shown in FIG. 4B overlaid with the frequency domain response 501 of the rectangular detector response shown in FIG. 3A. As seen in graph 500, the central frequency response 502 remains essentially unchanged; however, the higher frequency components 504 of the non-rectangular spatial domain response of FIG. 4B are reduced compared to the higher frequency components 506 of the rectangular spatial domain response shown in FIG. 3A. As explained previously, the high frequency components cause aliasing artifacts in the CT images. In this way, anti-aliasing shape of the post-patient collimator leads to a reduction in high frequency components detected by the detector. This, in turn, feeds forward and reduces the aliasing seen in the final clinical image. In this way, aliasing artifacts in the CT images may be reduced by incorporating an anti-aliasing shaped post-patient collimator without using focal spot wobble and/or any post-processing or digitization of the CT images, for example. Typically, post-processing is used to reduce aliasing. However, by performing the post-processing on signals that are not pre-filtered, overall signal levels of the system may be reduced. By pre-filtering the signals before they reach the detector, the overall signal levels may not be reduced in the imaging system. It may be appreciated that the analog pre-filtering of the signals using the anti-aliasing post-patient collimator is performed prior to any post-processing or digitization of the signals, and not after the signals have been digitally sampled. In this way, analog pre-filtering of the signals in the spatial domain using the anti-aliasing post-patient collimator reduces aliasing artifacts in the CT images.

The example embodiment described so far with reference to FIG. 3B includes incorporating the anti-aliasing shape to the post-patient collimator of the imaging system. In another embodiment, it may be possible to include the anti-aliasing shape in a collimator plate coupled to an anti-scatter leaf, as shown in FIG. 7.

Turning now to FIG. 7, a schematic view 700 of a detector 702 of an imaging system is shown. The detector 702 may be one non-limiting example of the detector array 108 shown in FIGS. 1 and 2 of the imaging system such as the imaging system 200 of FIG. 2. As described above, CT imaging systems include an x-ray source (such as the source 104 of FIGS. 1 and 2) that emits a fan-shaped beam toward a subject or object (such as the subject 204 of FIG. 2). The beam, after being attenuated by the subject, impinges upon an array of radiation detectors. The intensity of the attenuated beam radiation received at the detector array is typically dependent upon the attenuation of the x-ray beam by the subject. Herein, each detector element of the detector array produces a separate electrical signal indicative of the attenuated beam received by each detector element. The electrical signals are processed to generate a CT image of the subject.

The CT imaging system may include a collimator 704, scintillator cells 710, a reflector channel 712, and a photodiode (not shown in FIG. 7). Herein, the collimator 704 collimates the x-ray beams received at the detector 702 and the scintillator cell 710 converts the x-ray to light energies, and the photodiode receives the light energy from the scintillator and converts the light energy into electrical signals. As such, the output of the photodiodes is transmitted to image processing systems (such as image processing system 10 shown in FIG. 1) for image construction.

The collimator 704 includes an anti-scatter leaf 706 coupled to a collimator plate 708. Together, the anti-scatter leaf 706 and the collimator plate 708 absorb the scattered radiation and reduce noise in the system. In some examples, the collimator 704 may be composed of highly absorbing materials such as tungsten or lead. In other examples, the collimator 704 may be composed of aluminum. Herein, the anti-scatter leaf 706 and the collimator plate 708 may be composed of the same material, or different material.

FIG. 7 includes the Cartesian coordinate system, showing that the scintillator cells are spaced along the x axis. The leaf 706 extends along they axis (e.g., has a longitudinal axis parallel to the y axis). FIG. 7 may be a side view of the collimator, leaf, and detector (e.g., a head-on view while looking down the bore of the CT gantry). In other examples, FIG. 7 may be a cross-sectional view taken along the length of the collimator, leaf, and detector at a suitable plane of the z axis.

The collimator plate 708 may be aligned with the reflector channel 712 disposed between adjacent scintillator cells. In some examples, a width Wr of the reflector channel 712 between the scintillator cells may represent an inactive region, and a width Ws of the scintillator cell may represent an active region. The reflector material reduces light leaking into adjacent scintillator cells. The inventors have recognized that it may be possible to include an anti-aliasing shape to the collimator plate 708 to reducing aliasing artifacts in the CT images. As explained previously with reference to FIG. 3B, the anti-aliasing shape may modulate the x-ray beam reaching the scintillator 710, and thus reduce aliasing artifacts by pre-filtering the signals.

The anti-scatter leaf 706 may include a rectangular shape of length L3 and height H2 with H2>L3, where the leaf 706 extends uniformly in each axis of the coordinate system. A bottom of the anti-scatter leaf may be coupled to a top of the collimator plate 708. A magnified view 800 of the collimator plate 708 is shown in FIG. 8A. Tuning now to FIG. 8A, the collimator plate 708 has a bottom 804 of length L1, and a top 802 of length L2, parallel to each other, and separated by a thickness H1. In one example, the collimator plate 708 may be composed of aluminum. In such an example, for a monoenergetic beam of 80 keV, the thickness H1 of the collimator plate 708 may be 3 mm. The length L1 of the bottom 804 may be larger than the length L2 of the top 802. In one specific example, the length L1 may be 0.28 mm and the length L2 may be 0.15 mm. However, the length L2 may be larger than the length L3 of the anti-scatter leaf 706 shown in FIG. 7. Thus, L1>L2>L3.

The collimator plate 708 may include a first side 806 and a second side 808. The first and the second sides may not be straight, but may have an arc shape. In one example, the radius of curvature of both the first and the second sides may be the same. In another example, the radius of curvature of the first and the second sides may be different. Herein, a bottom of the first side 806 is separated at a distance L1 from a bottom of the second side 808, while a top of the first side 806 is at a distance L2 from a top of the second side 808. Together, the top 802, the bottom 804, the first side 806, and the second side 808 may form a "pi" shaped collimator plate 708. Hereafter, the collimator plate 708 may be referred to as an anti-aliasing collimator plate.

Mathematically, the anti-aliasing shape of the collimator plate 708 may be represented in 1-D by equation (5), as shown below:

$$t(x) = \begin{cases} H1, & |d| < \frac{X}{2} \\ 0, & |d| > \left(\frac{X}{2} + \delta\right) \\ \frac{-\ln\left[\left(\frac{L1}{2} - |d|\right) * \frac{H1}{\delta}\right]}{\mu}, & \text{else} \end{cases} \quad (5)$$

where t(x) represents the transition profile of the collimator plate, H1 represents the maximum height of the plate, d represents the transverse distance in mm, r μ represents the attenuation coefficient of the collimator plate 708 at the given energy and δ=(L1−L2)/2.

A transmission profile 850 of the collimator plate 708 is shown in FIG. 8B. As shown in FIG. 8B, the transmission profile 850 includes a trapezoidal shape. The x-axis represents the thickness in mm and the y-axis represents the transmission of the x-rays through the collimator plate 708. Herein, a transmission of 1 indicates 100% transmission, meaning all the x-ray beams are transmitted without any attenuation. A transmission of 0 indicates 0% transmission, implying that all the x-ray beams are blocked. A transmission of 0.5 indicated 50% transmission, implying that 50% of the incoming x-rays are blocked at the collimator plater, while a remaining 50% is transmitted through to the scintillator.

Due to the anti-aliasing shape of the collimator plate 708, the transmission profile of the collimator plate includes a trapezoidal shape. Herein, the arc shape of the first and the second sides of the collimator plate 708 allow a portion of the x-rays to transmit through while blocking a remaining portion of the x-rays. As the thickness of the first side and the second side increase, the amount of transmission through the sides decreases. At the full width half maximum of the collimator plate 708, about 50% of the x-ray beams are transmitted to the scintillator. In this way, the anti-aliasing shape of the collimator plate 708 modulates the signals passing through them. Consequently, higher frequency components of the signals are reduced as shown in FIG. 9. Before turning to FIG. 9, it may be noted that in some examples, the anti-aliasing shape may be incorporated to the scintillator material. For example, the scintillator material forming scintillator 710 may include a shape (such as an anti-aliasing shape as explained previously) that modulates the signals directly and filters the signals to reduce the high frequency components. This is in contrast to the collimator plate providing the modulation in previous examples. In this example, the scintillator material would be thinner at the edges of the cell and reach full thickness toward the center of the cell.

Turning to FIG. 9, a modulation transfer function (MTF) 900 of a detector having anti-aliasing collimator plates such as the anti-aliasing collimator plates 708 discussed in FIGS. 7, 8A, and 8B is shown. The MTF is used to describe the high contrast resolution performance of the detector. The MTF is a measure of the transfer of modulation from the subject to the image. The MTF 900 includes an MTF 902 of a first detector without an anti-aliasing collimator plate (shown in dashed lines), overlaid on an MTF 904 of a second detector having an anti-aliasing collimator plate (such as the anti-aliasing collimator plate 708 described in FIGS. 7 and 8A, shown in solid lines). The central response 906 of both the first and the second detectors remain essentially the same. However, there is a reduction in the side lobe areas (compare side lobe 908 of first detector with side lobe 910 of second detector). These side lobes cause spurious resolution and after digital sampling can wraparound to form aliasing artifacts, as well. Specifically, the second detector having the anti-aliasing collimator plate includes a 21.5% reduction in the side lobe area compared to the first detector without the anti-aliasing collimator. By reducing the side lobe area in the MTF, aliasing artifacts in the final CT images may be reduced. In this way, the anti-aliasing shape of the post-patient collimator plates reduces aliasing artifacts in the CT images. Aliasing artifacts in the CT images may be reduced by incorporating an ant-aliasing shape to the collimator plates without using additional methods such as focal spot wobble and/or any post-processing or digitization of the CT images, for example. Thus, analog pre-filtering of the signals may be achieved using the anti-aliasing collimator plate.

FIGS. 1, 2, 3, 4, 7, and 8A show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Turning now to FIG. 10, an example method 1000 for reducing aliasing artifacts in an imaging system is shown. Instructions for carrying out method 1000 herein may be executed by a processor (e.g., processor or computing device 216 of FIG. 2 and/or image processing unit 10 of FIG. 1) based on instructions stored on a memory of the processor and in conjunction with signals received from sensors of the imaging system, such as the sensors described above with reference to FIGS. 1-9. The processor may employ actuators of the CT imaging system to adjust the operation of the imaging system, the collimators, and the detectors, according to the methods described below.

Method 1000 begins at 1005 by initializing a scan sequence. In some examples, initializing the scan sequence may include powering up an x-ray source (such as the source 104 of FIGS. 1 and 2) and a detector array (such as detector array 108 of FIGS. 1 and 2) of an imaging system (such as imaging system 200 of FIG. 2). In addition, the processor may move a table on which a patient is lying in between the source and the detector array. Specifically, the controller may position of an anatomy of interest between the source and the collimator.

At 1010, the processor may detect pre-filtered analog signals at the detector array. In one example, post-patient collimators used in the imaging system may include an anti-aliasing shape, as explained with reference to FIG. 3B. Therein, the collimator includes a non-rectangular transition profile because of the curved shape of the collimator. As a result, the incoming primary radiation signals that are attenuated by the patient undergo amplitude modulation at the post-patient collimator, and high frequency components of the incoming signals are reduced. Thus, the analog signals are pre-filtered at the post-patient collimator having the anti-aliasing shape. It may be appreciated that the signal is filtered by passing the primary signal attenuated by the patient through the collimator. Herein, the collimator includes a first high attenuating regions and a second, low attenuating region, wherein the first region attenuates the primary signal by a higher amount than the second region.

Alternatively, the pre-filtering may be achieved by using collimator plates that have an anti-aliasing shape as shown in FIG. 7. Specifically, the collimator plates placed in contact with reflector material of the detector array may include a "pi" shape. As such, the "pi" shape of the collimator plate may modulate the radiation signals and pre-filter the signals reaching the detector, for example. Herein, the non-uniform profile of the collimator plate results in non-uniform attenuation of signals passing through the collimator plate. In the "pi" shape of the collimator plate, the center region may transmit uniformly, but non-uniformly across the entire width of the plate. It may be appreciated that the signal is filtered by passing the signal through the collimator having a collimator plate. The filtered signal may be generated by passing the primary signal through the collimator plate and to a scintillator of an assembly of the detector, wherein the collimator plate may include a non-rectangular shape with at least two curved sides.

At 1015, method 1000 includes receiving electrical signals from the photodiodes of the detector. As explained previously, scintillators may be included in the detector assembly to convert incoming x-ray radiation to light energies. Photo diodes then receive the light energies and generate electrical signals. The processor may receive the electrical signals at 1015.

Next at 1020, method 1000 includes generating CT images with reduced aliasing artifacts. As explained previously, aliasing in the final CT image is a common clinical problem. The aliasing artifacts are generally more pronounced in small joint (wrist, ankle/foot, knee), C-Spine, facial bones, and inner auditory canal scans. Since the detector cell is the main system limiter of resolution when imaging near the scan iso-center, if post-patient collimators with rectangular profiles are used, large aliasing side lobes occur in the frequency domain. However, by incorporating anti-aliasing collimators, aliasing at the detector during acquisition may be reduced, and thus aliasing artifacts in the images are reduced. Additionally, low levels of aliasing that are below the visually detectable threshold serve to increase the "structured" noise level of the image, so an aliasing reduction may lead to noise reductions in the system.

At 1025, method 1000 includes performing post-processing on the images and displaying the post-processed images. In some examples, the images may be digitized and post-processed. Some non-limiting examples of post-processing methods include two-dimensional multiplanar reformatting (MPR), volume rendering techniques such as virtual colonoscopy and tissue transition projection, and 3D rendering techniques such as shaded surface display and maximum intensity projection (MIP). Method 1000 ends.

Thus, the collimator, collimator plate, and methods described herein provide for a non-uniform attenuation of a source signal (e.g., radiation) at high-attenuating regions of a collimator or collimator plate. The non-uniform attenuation is achieved by not only interspersing of low-attenuating and high-attenuating regions, but also by the shape, material density, and/or orientation of the high-attenuating regions of collimator or collimator plates with respect to a detector array. The high-attenuation regions may be shaped, comprised of material, or oriented in such a manner that non-uniform attenuation of the source signal is provided to the detector (e.g., the high-attenuating regions provide a non-uniform, non-rectangular transmission profile of the source signal to the detector). In one example, the high-attenuating regions may have a non-uniform shape (e.g., extend non-uniformly along at least one axis), such as the collimator illustrated in FIG. 3B, therein providing both a non-rectangular transition profile and transmission profile. In other examples, the high-attenuating regions may be have non-uniform density, such that a non-rectangular transmission profile is provided, even if the high-attenuating regions are rectangular in overall shape. Further, the high-attenuating regions may be rotated with the respect to the detector array, such that at least in cross-section, the high-attenuating regions are non-rectangular. In this way, the anti-aliasing post-patient collimator and anti-aliasing collimator plates may serve as analog pre-filters that reduce aliasing artifacts without performing adjustments such as adjusting a focal spot of the source or adjusting a shape of the detector cell, for example. In some examples, the collimator and/or collimator plates described herein may be manufactured using an additive process.

A technical effect of the disclosure is that the analog pre-filtering of the signals is achieved in the continuous, spatial domain, not after the signals have been digitized.

The systems and methods described above also provide for a method for an imaging system, the method comprising receiving a filtered signal generated by passing a primary signal through a collimator having a non-rectangular transition profile, the collimator positioned between an object and a detector of the imaging system, and generating an image based on the filtered signal received at the detector. In a first example of the method, the method may additionally or alternatively include wherein the primary signal including radiation from a source of the imaging system attenuated by the object placed between the source and the detector, and wherein receiving the filtered signal generated by passing the primary signal through the collimator comprises receiving the filtered signal generated by passing the primary signal through each of a first region and a second region of the collimator, the first region attenuating the primary signal by a higher amount than the second region. A second example of the method optionally includes the first example, and further includes wherein a level of transmission of the primary signal through the collimator is based on a shape of the first region, the shape being non-rectangular, thereby to reduce aliasing artifacts in the image. A third example of the method optionally includes one or more of the first and the second examples, and further includes wherein a level of transmission of the primary signal through the first region is approximately inversely proportional to a first height of the first region and a level of transmission of the primary signal through the second region is directly proportional to a second height of the second region. As used herein, the level of transmission of the primary signal through the first region being approximately inversely proportional to the first height of the first region may include the level of transmission for a given location of the first region being a rough first order approximation. The level of transmission is fully described by the equation:

$$\text{attenuation}(E) = \int_{E}^{\infty} \varphi(E) \exp[-\mu(E) l]$$

Where mu is the linear attenuation coefficient (which changes with energy and material), phi is the normalized spectrum, and l is the length.

A fourth example of the method optionally includes one or more of the first through the third examples, and further includes wherein the non-rectangular transition profile of the collimator generates a trapezoidal shaped detector response. A fifth example of the method optionally includes one or more of the first through the fourth examples, and further includes receiving the filtered signal prior to performing one or more of post-filtering and digitization of the primary signal. A sixth example of the method optionally includes one or more of the first through the fifth examples, and further includes wherein the post-filtering includes one or more of two-dimensional multiplanar reformatting (MPR), virtual colonoscopy, tissue transition projection, shaded surface display, and maximum intensity projection, and wherein the collimator includes scatter rejection properties.

The systems and methods described above also provide for a collimator for a medical imaging system, the collimator comprising a plurality of high attenuating regions interleaved with a plurality of low attenuating regions, each high attenuating region having a non-uniform transition profile and configured to be aligned with a respective inactive region of a respective channel of a detector of the medical imaging system. In a first example of the collimator, the collimator may additionally or alternatively include wherein each region of the plurality of high attenuating regions includes a first, non-rectangular shape. A second example of the collimator optionally includes the first example and further includes wherein the plurality of low attenuating regions are void of material. A third example of the collimator optionally includes one or more of the first and the second examples, and further includes wherein the first shape includes one or more of a bell shape, a dome shape, and a sinusoidal shape. A fourth example of the collimator optionally includes one or more of the first through the third examples, and further includes wherein a level of attenuation of signals in the medical imaging system by the plurality of high attenuating regions is based on one the first shape. A fifth example of the collimator optionally includes one or more of the first through the fourth examples, and further includes wherein a level of transmission of signals in the medical imaging system by the low attenuating regions is based on the first shape. A sixth example of the collimator optionally includes one or more of the first through the fifth examples, and further includes wherein each region of the plurality of low attenuating regions is aligned with a respective active region of a respective channel of the detector. A seventh example of the collimator optionally includes one or more of the first through the sixth examples, and further includes wherein each region of the plurality of high attenuation regions is composed of one or more of tungsten and lead.

The systems and methods described above also provide for a system, the system, comprising an x-ray source configured to project a beam of x-rays towards a patient, an array of detectors configured to receive an attenuated beam passing through the patient, and a collimator inserted between the patient and the array of detectors and configured to non-uniformly attenuate the beam, the collimator having bell shaped plates each separated by a gap. In a first example of the system, the system may additionally or alternatively include wherein the array of detectors is configured to receive the beam passing through the collimator and generate a signal based on an amount of beam reaching the array of detectors, the amount based on a curvature of the bell shaped plates of the collimator. A second example of the system optionally includes one or more of the first and the second example, and further includes a processor configured with instructions in non-transitory memory that when executed cause the processor to: generate an image based on the signal, the signal being filtered by the bell shaped plates of the collimator. A third example of the system optionally includes one or more of the first and the second examples, and further includes wherein the amount of the beam reaching the array of detector is inversely proportional to a height of the bell shaped plates and wherein the amount of beam passing through the gap is higher than the amount of beam passing through the plurality of bell shaped plates. A fourth example of the system optionally includes one or more of the first through the third examples, and further includes wherein the bell shaped plates are composed of one or more of tungsten and lead.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

As used herein, the phrase "pixel" also includes embodiments of the invention where the data is represented by a "voxel." Thus, both the terms "pixel" and "voxel" may be used interchangeably herein.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
providing a source that emits radiation, a detector, and a collimator having bell shaped plates each separated by a gap that provides the collimator with a non-rectangular curved transition profile including a non-uniform width and a non-uniform height;
receiving at the detector a filtered and modulated signal generated by passing a primary signal through the collimator having bell shaped plates each separated by the gap that provides the collimator with the non-rectangular curved transition profile including the non-uniform width and the non-uniform height, the collimator positioned between an object and the detector; and
generating an image based on the filtered and modulated signal received at the detector.

2. The method of claim 1, wherein the primary signal includes radiation from the source of the imaging system attenuated by the object placed between the source and the detector, wherein receiving the filtered and modulated signal generated by passing the primary signal through the collimator comprises receiving the filtered and modulated signal generated by passing the primary signal through each of a first region and a second region of the collimator, wherein the first region attenuates the primary signal by a higher amount than the second region, and wherein the filtered and modulated signal is non-uniform.

3. The method of claim 1, wherein the non-rectangular transition profile of the collimator generates a trapezoidal shaped detector response.

4. The method of claim 1, further comprising receiving the filtered signal prior to performing one or more of post-filtering and digitization of the primary signal.

5. The method of claim 2, wherein a level of transmission of the primary signal through the collimator is based on a shape of the first region, the shape being non-rectangular, thereby to reduce aliasing artifacts in the image.

6. The method of claim 2, wherein a level of transmission of the primary signal through the first region is inversely proportional to a first height of the first region and a level of transmission of the primary signal through the second region is directly proportional to a second height of the second region.

7. The method of claim 4, wherein the post-filtering includes one or more of two-dimensional multiplanar reformatting (MPR), virtual colonoscopy, tissue transition projection, shaded surface display, and maximum intensity projection, and wherein the collimator includes scatter rejection properties.

8. A medical imaging system, comprising:
an x-ray source configured to project a beam of x-rays towards a patient;
an array of detectors configured to receive an attenuated beam passing through the patient; and
a collimator inserted between the patient and the array of detectors and configured to non-uniformly attenuate and modulate the beam, the collimator having bell shaped plates each separated by a gap;
wherein the bell shaped plates each separated by a gap provides the collimator with a non-rectangular curved transition profile.

9. The medical imaging system of claim 8, wherein the array of detectors is configured to receive the modulated beam passing through the collimator and generate a signal based on an amount of beam reaching the array of detectors, the amount based on a curvature of the bell shaped plates of the collimator.

10. The medical imaging system of claim 8, wherein the bell shaped plates are composed of one or more of tungsten and lead.

11. The medical imaging system of claim 9, further comprising a processor configured with instructions in non-transitory memory that when executed cause the processor to:
generate an image based on the signal, the signal being filtered and modulated by the bell shaped plates of the collimator.

12. The medical imaging system of claim 9, wherein the amount of the beam reaching the array of detector is inversely proportional to a height of the bell shaped plates and wherein the amount of beam passing through the gap is higher than the amount of beam passing through the bell shaped plates.

* * * * *